US00PP11227P

United States Patent [19]

Walden

[11] Patent Number: Plant 11,227

[45] Date of Patent: Feb. 15, 2000

[54] MINIATURE ROSE PLANT NAMED 'JACSTRIP'

[75] Inventor: John K. Walden, Thousand Oaks, Calif.

[73] Assignee: Bear Creek Gardens, Inc., Medford, Oreg.

[21] Appl. No.: 09/009,795

[22] Filed: Jan. 20, 1998

[51] Int. Cl.[7] ..... A01H 5/00

[52] U.S. Cl. ..... Plt./116

[58] Field of Search ..... Plt./116, 122, 123, Plt./129

[56] References Cited

U.S. PATENT DOCUMENTS

| | | | |
|---|---|---|---|
| P.P. 5,145 | 11/1983 | Saville | Plt./116 |
| P.P. 5,176 | 1/1984 | Williams | Plt./116 |
| P.P. 5,791 | 10/1986 | Moore | Plt./116 |

*Primary Examiner*—Howard J. Locker

*Attorney, Agent, or Firm*—Klarquist Sparkman Campbell Leigh & Whinston, LLP

[57] ABSTRACT

Miniature rose plant having long lived striped red and yellow flowers, disease resistant foliage, compact growth habit, and long shelf life when grown as a pot rose.

1 Drawing Sheet

The present invention relates to a new and distinct variety of rose plant of the miniature class which was originated by me by crossing an unnamed seedling, with the variety 'SAValife', U.S. Plant Pat. No. 5,482.

The primary objective of this breeding was to produce a new miniature rose variety having the striped flowers and disease resistant foliage of the unnamed female parent combined with the compact plant habit and the bright, clear yellow and red flower color and flower form of the male parent. The objective was substantially achieved, along with other desirable improvements, as evidenced by the following unique combination of characteristics that are outstanding in the new variety and that distinguish it from its parents, as well as from all other varieties of which I am aware:

1. Striped, red and yellow blooms;
2. Disease resistant foliage;
3. Compact plant habit;
4. Very long shelf life as a pot rose; and
5. Color change as the flower ages to a pleasant pink and light pink striped flower.

Asexual reproduction of this new variety by cutting propagation, as performed at Somis, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

In such illustration, the five blooms shown at the top left are blooms as viewed from above in the following stages starting with the bloom farthest right:

Bloom on day one starting to open;
Bloom on day two;
Bloom on day three;
Bloom on day four;
Bloom on day seven or eight.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—Unnamed seedling.

*Pollen parent.*—'SAValife' (U.S. Plant Pat. No. 5,482).

Classification:

*Botanical.*—*Rosa hybrida.*

*Commercial.*—Miniature rose.

FLOWER

Observations made from specimens grown in a greenhouse environment at Somis, Calif. from September, 1994 to September, 1997.

Blooming habit: Continuous.

Bud:

*Size.*—Seven-sixteenths to one-half inch when the petals start to unfurl.

*Form.*—The bud form is short, blunt topped, broad based.

*Color.*—When sepals first divide, bud color is Yellow-orange Group 19C and Red Group 46B. When half blown, the upper sides of the petals are Red Group 46C or Yellow Group 6C to a combination thereof; and the outer portions of the lower sides of the petals are Yellow Group 2C or Red Group 53C but predominantly Yellow Group 12D or any combination thereof, and are predominantly Yellow Group 2C on the inner half of the petal.

*Sepals.*—Color: Yellow-green group 144A. Surface texture: Smooth to slightly hairy, with few very fine hairs. There are three very lightly appendaged sepals. There are two unappendaged sepals with hairy edges.

*Receptacle.*—Color: Yellow-green Group 144B. Shape: Funnel. Size: Broad, small. Surface: Smooth, glandular.

*Peduncle.*—Length: Medium (1⅜"–1½"). Surface: Smooth, glandular, and hairy. Color: Medium green (Green Group 143C). Strength: Erect.

*Opening.*—Buds open with a low center to a flat then slightly mounded flower, petals are slightly folded along the midline, then lay nearly flat near flower finish.

Bloom:

*Size.*—Small. Average open size is 1¼ to 1⅜ inches.

*Borne.*—Singly and in small, pyramidal clusters of three to seven flowers.

*Stems.*—Short to normal.

*Form.*—When first open: Flat. Permanence: Outer petal edges curl slightly.

*Petalage.*—Number of petals under normal conditions: 55–65.

*Color.*—The upper sides of the petals are Yellow Group 5C on the inner half with striping of Red Group 45B and Red Group 54A. The reverse sides of the petals are generally Yellow Group 5C with some areas of Red Group 49D with stripes of Red Group 53C throughout. The base of each petal has a small half moon of Yellow Group 5C. The major color on the upper sides of some petals is Red Group 53C, on others it is Red Group 54B.

*Variegations.*—Flower color varies with each flower from nearly all Red Group 53C to Red Group 54B.

*Discoloration.*—At the end of the first day: No change. At the end of the third day: A general lightening of yellow shaded areas and an increase of Red Group 54A areas.

*Fragrance.*—Slight.

Petals:

*Texture.*—Thin, leathery.

*Shape.*—Deltoid on outer petals, round as progressing inward and oval near the center of the flower. All petals are pointed.

*Form.*—Tips slightly recurved.

*Arrangement.*—Imbricated. Petaloids in the center are few.

*Persistence.*—*Hang on and dry, eventually drop.*

*Lastingness.*—On the plant: Very long (17–21 days). As a cut flower: Very long.

Reproductive parts:

*Anthers.*—Size: Small. Quantity: Few. Color: Yellow. Arrangement: Mixed with petaloids.

*Filaments.*—Color: White to yellow.

*Pollen.*—Color: Lemon yellow.

*Styles.*—Color: Yellow Group 11D with slight reddish immediately below stigma.

*Stigmas.*—Color: Greenish-white.

Plant:

*Form.*—Miniature bush.

*Growth.*—Dwarf; upright; branching; compact.

Foliage: Number of leaflets on normal mid-stem leaves: Five, occasionally seven.

*Size.*—Small (3½" long×1⅝" wide).

*Quantity.*—Abundant.

*Color.*—New foliage: Upper surface: Yellow-green Group 146C with a hint of bronze (Greyed-red Group 181A). Lower surface: Greyed-red Group 181A. Old foliage: Upper surface: Close to Green Group 137A. Lower surface: Yellow-green Group 147B.

*Shape.*—Elliptic.

*Texture.*—Upper side: Leathery, smooth.

*Edge.*—Serrated.

*Serration.*—Single.

*Petiole rachis.*—Color: Green.

*Petiole underside.*—Rough with prickles.

*Stipules.*—Short, glandular, serrated.

*Disease resistance.*—Resistant to mildew under normal growing conditions in the greenhouse at Somis, Calif.

Wood:

*New wood.*—Color: Light green (Green Group 143). Bark: Smooth.

*Old wood.*—Color: Green (Yellow-green Group 146A). Bark: Smooth.

Prickles:

*Quantity.*—On main canes from base: Ordinary to few. On laterals from main canes: Few.

*Form.*—Medium (¼").

*Color when young.*—Transparent to translucent.

Small prickles:

*Quantity.*—On main stalks: Few. On laterals: None.

*Color.*—Green.

I claim:

1. A new and distinct variety of miniature rose plant as herein shown and described characterized particularly by its striped red and yellow flowers which change as the flower ages to a pleasant pink and light pink striped flower, its disease resistant foliage, compact growth habit, and very long shelf life when grown as a pot rose.

* * * * *

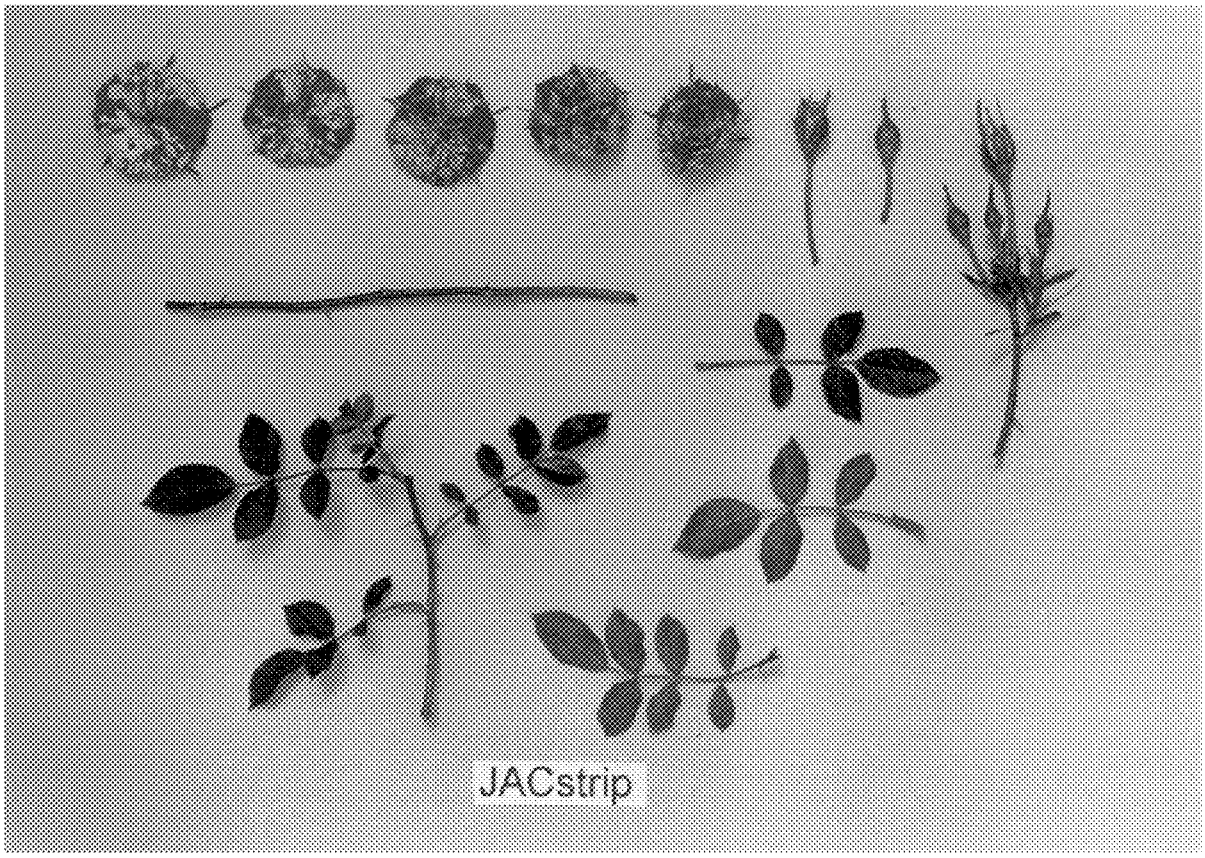
JACstrip